United States Patent [19]

Knöfel et al.

[11] Patent Number: 5,672,737

[45] Date of Patent: Sep. 30, 1997

[54] FRACTIONATION AND PURIFICATION OF MIXTURES OF AROMATIC POLYAMINES AND USE THEREOF

[75] Inventors: Hartmut Knöfel, Odenthal; Michael Brockelt, Leverkusen, both of Germany

[73] Assignee: Bayer Aktiengesellschaft, Leverkusen, Germany

[21] Appl. No.: 623,285

[22] Filed: Mar. 28, 1996

[30] Foreign Application Priority Data

Apr. 7, 1995 [DE] Germany ............... 195 13 119.3

[51] Int. Cl.[6] .................................................. C07C 209/86
[52] U.S. Cl. .................. 560/347; 564/315; 564/331; 564/332; 564/333; 564/334; 564/437; 564/450; 564/451
[58] Field of Search ............... 564/315, 331, 564/332, 333, 334, 437, 450, 451; 560/347

[56] References Cited

U.S. PATENT DOCUMENTS

| 4,087,459 | 5/1978 | Knöfel et al. | 564/331 |
|---|---|---|---|
| 4,914,236 | 4/1990 | Knöfel et al. | 564/334 |
| 4,924,028 | 5/1990 | Knofel et al. | 564/331 |
| 5,196,591 | 3/1993 | Knofel et al. | 564/331 |
| 5,359,141 | 10/1994 | Knofel et al. | 564/331 |

FOREIGN PATENT DOCUMENTS

| 31423 | 7/1981 | European Pat. Off. . |
|---|---|---|
| 161600 | 11/1985 | European Pat. Off. . |
| 2238319 | 2/1973 | Germany . |
| 1170619 | 11/1969 | United Kingdom . |

*Primary Examiner*—Richard L. Raymond
*Attorney, Agent, or Firm*—Jospeh C. Gil

[57] ABSTRACT

The invention relates to a process for the fractionation and purification of mixtures of aromatic polyamines and to the use thereof.

14 Claims, 4 Drawing Sheets and

FRACTIONATION AND PURIFICATION OF MIXTURES OF AROMATIC POLYAMINES AND USE THEREOF

BACKGROUND OF THE INVENTION

The invention present relates to a process for the fractionation and purification of mixtures of aromatic polyamines and to the use thereof.

The preparation of aromatic polyamines and mixtures of aromatic polyamines, especially of the diphenylmethane series, is described in numerous patent applications and patents. Of outstanding importance here is the use of these products as raw materials for the preparation of isocyanates, normally by reaction of the polyamine mixtures with phosgene using the generally conventional and known methods.

In many cases, however, the resulting isocyanates or isocyanate mixtures are not obtained in the form and with the composition that are preferable for further use at the isocyanate stage, but must first be converted to the usable form by working-up and separation processes which are sometimes expensive. Suitable polyamine precursors which can be converted more cheaply to the forms usable for isocyanates are in many cases difficult or impossible to obtain in terms of process engineering or the economics of their preparation are unattractive.

An example is the preparation of the 4,4'-diisocyanatodiphenylmethane important for the manufacture of high-quality polyurethane materials, whose amine precursor can normally be obtained from aniline and formaldehyde only together with isomers, especially the 2,4'-isomer, and higher-functional polyamines. Although these constituents are the basis for isocyanates which are also desirable, separation of the crude isocyanates into the isocyanates or isocyanate mixtures suitable for further use is not easy.

The normal procedure is first to separate some of the dinuclear compounds from the rest. The 4,4'-diisocyanatodiphenylmethane is then separated from the other isomers in the dinuclear fraction in a second distillation step requiring many separation stages.

In more recent times the 2,4'-isomer in enriched form has itself become increasingly important as a polyurethane raw material, but considerable distillation costs are involved in enriching it relative to the 4,4'-isomer and separating it from the 2,2'-isomer which may be present. Isomer separation processes or enrichment processes within the fraction of the higher-nuclear homologues or higher-functional constituents of the amines, or of the isocyanates of the diphenylmethane series, are practically unknown.

There is also increasing interest in 4,4'-diaminodiphenylmethane as a raw material for di(4-isocyanatocyclohexyl)methane, the ring-hydrogenated form of 4,4'-diisocyanatodiphenylmethane, it being very expensive to prepare suitable mixtures of aromatic polyamines for the hydrogenation stage with the highest possible content of 4,4'-diaminodiphenylmethane and at the same time the lowest possible proportion of 2,4'-diaminodiphenylmethane.

It is known that amines can be separated in certain cases by partial conversion to their salts, utilizing inter alia the different basic strengths. This normally applies to monoamines with very different basic strengths. Again for mixtures of aromatic polyamines, especially of the diphenylmethane series, such disproportionation effects have already been described in two-phase systems (German Auslegeschriften 2,238,319 and 2,528,694).

Due to the numerous components present in such a mixture whose amino groups hardly differ in type—practically all are arylamino groups—the effects are not sufficiently great and pronounced to be of interest for direct use with simple agents.

The object of the present invention was to provide a process which made it possible easily to fractionate and purify mixtures of aromatic polyamines to give isomers in pure form or in enriched form.

DESCRIPTION OF THE INVENTION

Figure 1:
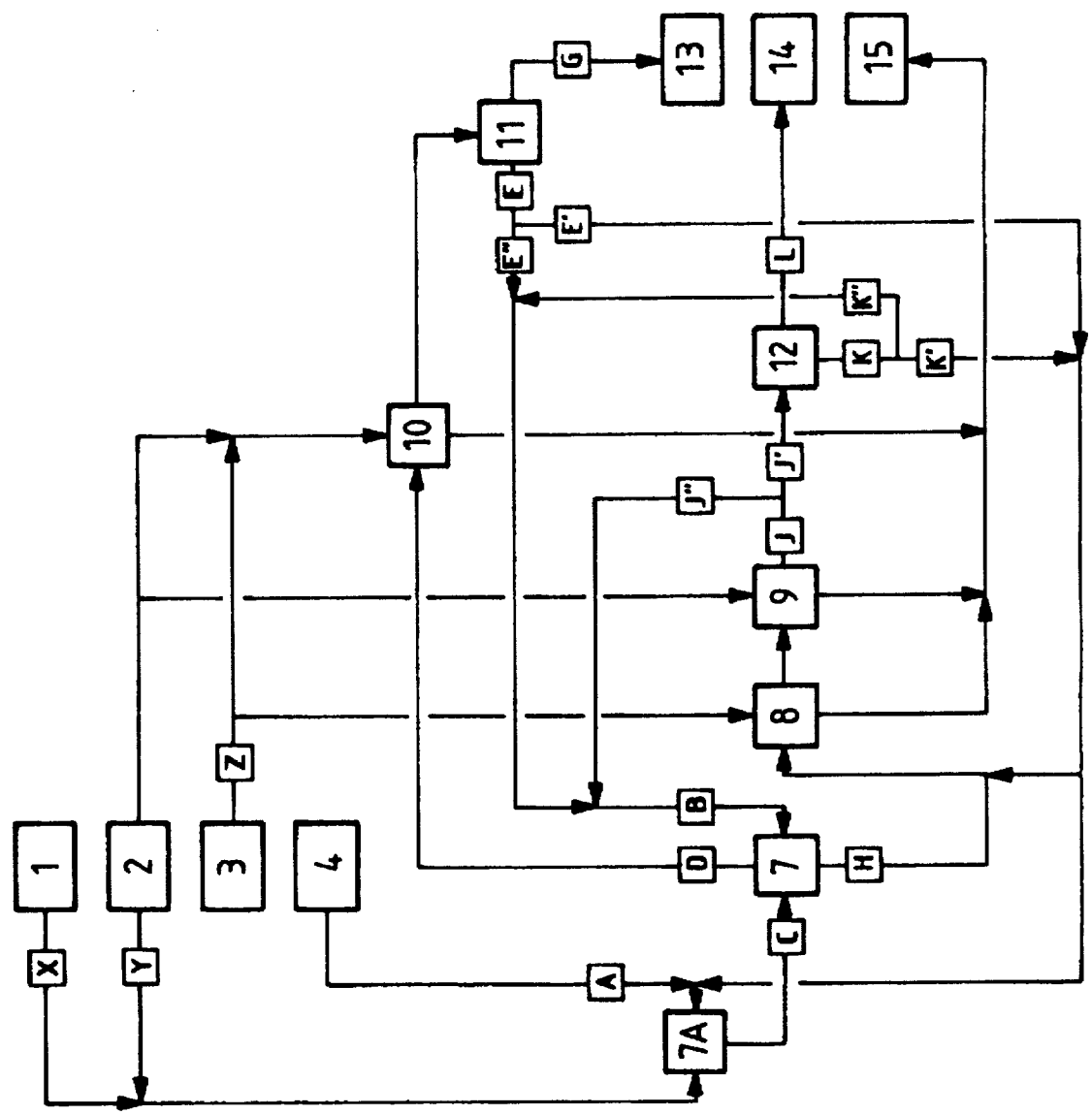
FIGS. 1 through 4 represent flow diagrams for embodiments of the present invention.

The above noted object was achieved by the process according to the invention, which attains a surprisingly high separation efficiency in the fractionation of mixtures of aromatic polyamines, especially of the diphenylmethane series, and whose effect well exceeds the known effects of the state of the art.

Other polyamine mixtures of different composition are obtained in the fractionation according to the invention of mixtures of aromatic polyamines. These derived polyamine mixtures may be ones which can only be obtained at very great cost by known synthetic routes. They may also be polyamine mixtures which are more suitable for a simplified preparation of isocyanates than the known polyamine mixtures which are technically easy to prepare, e.g. by anticipating at the amine stage isomer separations which are difficult to carry out at the isocyanate stage. By being impossible to prepare according to the state of the art, such mixtures can also be completely novel polyamine mixtures, which lead to completely novel isocyanates.

On the other hand, the process according to the invention can be utilized for obtaining product fractions corresponding to the standard or to the starting polyamines from any desired polyamine mixtures, i.e. including those recovered from the recycling of polyurethane plastics, which differ from the original polyamines or isocyanates used due to contamination or non-statistical (i.e. selective) losses of individual components in the recovery.

Finally, the process according to the invention can be utilized for co-fractionating by-products and intermediates arising from the synthesis and not desired in the end product, depleting them in one product fraction and correspondingly enriching them in another, and optionally removing them in a separate fraction.

The present invention relates to a broadly applicable process which makes it possible to achieve the object of fractionating and purifying mixtures of aromatic diamines and polyamines, especially of the diphenylmethane series.

The invention provides a process for the fractionation and purification of mixtures of aromatic polyamines, especially mixtures of polyamines of the diphenylmethane series, which is characterized in that a) the starting polyamine mixture (A) is partitioned in a two-phase system consisting of (i) a hydrophobic solvent phase (B) consisting essentially of aromatic auxiliary amine, which is sparingly soluble in water and whose boiling point under normal pressure is at least 20° C. below the boiling point of the lowest-boiling component of the starting mixture, and optionally polyamines, and (ii) an aqueous phase (C) consisting essentially of an aqueous solution of a strong acid and optionally auxiliary amine present at least partially in the salt form, and/or optionally polyamines present at least partially in the sail form, with the aid of an extraction stage (7) operating according to the countercurrent principle, and with thorough mixing of the 5 phases, the starting polyamine mixture being introduced into the extraction stage (7) with the aqueous phase (C), with the proviso that, in this two-phase system, the amine equivalents introduced into the streams (A), (B) and (C) are always in excess of the number of acid equivalents introduced into the stream (C), and the organic phase (D) leaving this extraction stage is separated, b) optionally at least partially via an intermediate extraction stage (6) and/or c) optionally with separation of a partial stream before or after passage through the extraction stage (6), if appropriate, and recycling of the separated partial stream, via an upstream extraction stage (5), at least partially into the extraction stage (7), d) after passage through a washing stage and/or neutralization stage (10), in a distillation stage (11), which is optionally operated as a multiple stage, into a distillate fraction, consisting essentially of auxiliary amine, and a first polyamine fraction, obtained as the distillation residue (G), e) the aqueous phase (H) leaving the extraction stage (7) is introduced into a neutralization stage (8), the acid contained in the aqueous phase is neutralized with bases, preferably aqueous sodium hydroxide solution, and the resulting product is then mechanically separated, in a phase separation step, into an aqueous phase, containing the acid in the form of its neutral salts, and an organic phase, containing essentially polyamine and auxiliary amine, and f) the organic phase (J) obtained in the neutralization stage (8) is optionally passed through a washing stage (9) and is at least partially worked up, in an optionally multiple distillation stage (12), into a distillate fraction (K), containing essentially auxiliary amine, and a second polyamine fraction, obtained as the distillation residue (L).

The numbers and capital letters used above and in the description which follows refer to elements and streams in the drawings.

The process is preferably carried out in such a way that b) the organic phase (D) obtained in the extraction stage (7) is at least partially extracted in an intermediate extraction stage (6) in countercurrent with at least part of the aqueous acid (stream X) and/or optionally water from the stream (Y) and/or optionally auxiliary amine, and/or extracted in countercurrent with at least part and preferably all of the aqueous phase (Q) obtained in the upstream extraction stage (5), if present, the aqueous phase (N) resulting from the intermediate extraction stage (6) is fed into the extraction stage (7), and the organic phase (O) obtained in the intermediate extraction stage (6) is fed into the working-up stage The process according to the invention is particularly preferably carried out in such a way that c) a partial stream of the organic phase (D) leaving the extraction stage (7), and/or a partial stream of the organic phase (O) leaving the intermediate extraction stage (6), if present, are separated off and, in an upstream extraction stage (5), reacted in one stage or, preferably, extracted in several stages in countercurrent with at least part of the aqueous acid available as the stream (X), the organic stream (P) used in the extraction stage (5) is proportioned so that, in (5), the greatest possible amount of the polyamine contained in said organic stream (P) passes into the aqueous phase (Q), the aqueous phase (Q) resulting from the upstream extraction stage (5) is fed into the extraction stage (6), optionally after the addition of water from the stream (Y) and/or auxiliary amine, and the polyamine-depleted organic phase (R) obtained in the upstream extraction stage (5) is at least partially fed into the extraction stage (7).

More particularly, the present invention, in its broadest embodiment, is directed to a process for the fractionation and purification of aromatic polyamine mixtures, in particular of polyamine mixtures of the diphenylmethane series, comprising:

a) mixing the polyamine starting mixture (A) in a first extraction stage (7) with a two-phase system comprising (i) a hydrophobic solvent phase (B) which consists essentially of an aromatic auxiliary amine which is slightly soluble in water and exhibits at normal pressure a boiling point which is at least 20° C. below the boiling point of the lowest-boiling component of the starting mixture, and optionally polyamine, and (ii) an aqueous phase (C) consisting essentially of water, a strong acid and optionally an auxiliary amine present at least in part in the salt form, and optionally polyamines present at least in part in the salt form, with said first extraction stage (6) operating on the countercurrent principle, and wherein said polyamine starting mixture (A) is introduced into said first extraction stage with said aqueous phase (C), with the proviso that the sum of amine equivalents introduced via polyamine mixture (A), hydrophobic solvent phase (B) and aqueous phase (C) always exceeds the number of acid equivalents introduced via aqueous phase (C), and with the further proviso that a first aqueous phase (H) and a first organic phase (D) exit said first extraction stage (6), b) distilling said first organic phase (D) in first distillation stage (11) into i) a first fraction (E) consisting essentially of auxiliary amine, and ii) a distillation residue (G) consisting essentially of a first polyamine fraction, c) neutralizing said first aqueous phase (H) by adding a base thereto (8) and phase separating the resultant mixture into i) a second aqueous phase containing the acid in the form of its neutral salt, and ii) a second organic phase consisting essentially of polyamine and auxiliary amine, and d) separating said second organic phase in a second distillation stage (12) into i) a distillate (K) consisting essentially of auxiliary amine, and ii) a distillation residue (L) consisting essentially of a second polyamine fraction.

The auxiliary amines used are generally monoamines such as aniline and/or aniline derivatives carrying substituents. The substituents are preferably $C_1$–$C_2$-alkyl substituents and/or benzyl radicals on the ring and/or on the nitrogen of the parent aniline. These substances can be used in pure form, in the form of isomer mixtures or in the form of technical-grade or specifically prepared mixtures with one another. Examples of suitable amines are N-propylaniline, N,N-dipropylaniline, N-butylaniline, N,N-dibutylaniline, N-isobutylaniline, 2-methylaniline, 2,4-dimethylaniline, N,2-dimethylaniline, N,N,2-trimethylaniline, N-ethyl-2-methylaniline, 3-methylaniline, N,N,3-trimethylaniline, N-ethyl-3-methylaniline, N,N-diethyl-3-methylaniline, N-butyl-3-methylaniline, 3-trifluoromethylaniline, 4-methylaniline, N,4-dimethylaniline, N,N,4-trimethylaniline, N-ethyl-4-methylaniline, N,N-diethyl-4-methylaniline, 2-ethylaniline, 4-ethylaniline, xylidines, 2-isopropylaniline, 2-ethyl-6-methylaniline, 2,4,5-trimethylaniline, 2,3,5-trimethylaniline, 4-tert-butylaniline, 2-ethyl-4,6-dimethylaniline, 2,6-diethyl-4-methylaniline, 2,6-diisopropylaniline, 4-cyclohexylaniline, 4-cyclohexyl-2-methylaniline, 2-methoxyaniline, 2-methoxy-N,N-dimethylaniline, 2-trifluoromethylaniline, 2-ethoxyaniline, 3-methoxyaniline, ethoxyaniline, 3-ethoxy-N,N-diethylaniline, 4-methoxyaniline, N-methyl-p-anisidine, 5-methoxy-2-methylaniline, 2-methoxy-5 -methylaniline, 2-ethoxy-5-methylaniline, 2,4-dimethoxyaniline, 2,5-dimethoxyaniline and 5,6,7,8-tetrahydro-1 (or 2)-naphthylamine. The following are preferably used as auxiliary amines: aniline, 2,6-dimethylaniline, 2,6-diethylaniline, 2-methyl-6-ethylaniline, mesidine, N-methylaniline, N-ethylaniline, N, N-dim ethylaniline, N, N-diethylaniline and aminodiphenylmethane.

The mixtures of polyamines of the diphenylmethane series which are preferably used are those obtained in the acid-catalyzed aniline/formaldehyde condensation.

The polyamine mixtures treated in this way, i.e. the fractions produced by the process according to the invention, are used for the preparation of the corresponding mixtures of aromatic polyisocyanates and for the manufacture of polyurethane plastics. The fractions produced by the process according to the invention can also be used for the preparation of the corresponding ring-hydrogenated polyamines or as crosslinking agents and epoxy hardeners. The corresponding polyisocyanates prepared from the fractionated polyamine mixtures are preferably used for the manufacture of polyurethane foams.

Starting mixtures are for example technical-grade arylamine mixtures such as those obtained in the preparation from the starting compounds or in the recovery. Examples of starting arylamine mixtures for whose fractionation and purification the process according to the invention is particularly suitable are 1. mixtures of polyamines of the diphenylmethane series such as those formed in the condensation and acid-catalyzed rearrangement of aniline with formaldehyde,
2. mixtures of polyamines of the diphenylmethane series such as those obtained in the acid-catalyzed condensation of substituted anilines with formaldehyde,
3. mixtures of polyamines of the diphenylmethane series such as those obtained in the mixed condensation of substituted anilines with one another and/or aniline with formaldehyde,
4. mixtures of polyamines of the diphenylmethane series such as those obtained in the condensation as well as mixed condensation of substituted anilines and/or aniline with aldehydes and/or ketones,
5. mixtures of polyamines of the diphenylmethane series such as those formed in the nitration and subsequent reduction of diarylmethanes and/or polyarylmethanes and/or substituted diarylmethanes and/or polyarylmethanes, polyarylmethanes being understood here as meaning especially the benzyl homologues of diphenylmethane,
6. mixtures of polyamines of the diphenylmethane series such as those formed in the condensation of monoaryl-monoamines (e.g. aniline, substituted anilines) and/or monoaryldiamines (phenylenediamines, substituted phenylenediamines)with aldehydes and ketones, especially formaldehyde, and acid-catalyzed rearrangement, and
7. mixtures of polyamines of the triphenylmethane series such as those formed e.g. in the nitration and subsequent reduction of triphenylmethane, especially alkyl-substituted triphenylmethanes, and its higher-nuclear homologues, especially benzyl homologues.

The acids used are water-soluble protonic acids with a pKa below 2.5, preferably below 1.5, examples being hydrochloric acid, hydrobromic acid, sulfuric acid, trifluoroacetic acid, methanesulphonic acid or phosphoric acid. It is preferable to use hydrochloric acid and sulfuric acid. The acids can also be used in a mixture with acid or neutral salts of such acids, e.g. the corresponding ammonium salts or else the corresponding alkali metal salts. In general, the acids are present in the aqueous phase (C), either as an aqueous solution of the free acid, or as an aqueous solution which also contains, in addition to the free acid, the ammonium salts of the acid with auxiliary amine and/or polyamine, or as an aqueous solution in which the acid is present entirely in the form of its ammonium salts with auxiliary amine and/or polyamine and which optionally contains further auxiliary amine not bound in the form of a salt.

At the latest after passage through the extraction stage (7), said acids are present in the aqueous phase in the form of the ammonium salts of the acid with the polyamine fraction present in the aqueous phase and with auxiliary amine.

After passage through the extraction stage or, if appropriate, extraction stages, the acid present in the aqueous phase is converted to the corresponding neutral salts by neutralization with strong bases, the polyamines and auxiliary amine bound in the form of salts being freed in this process.

The process according to the invention can be carried out either batchwise or continuously. Continuous operation is the preferred embodiment, the process being carried out in all stages under the autogenous pressure of the system and preferably in an inert gas atmosphere (nitrogen).

Figure 2:
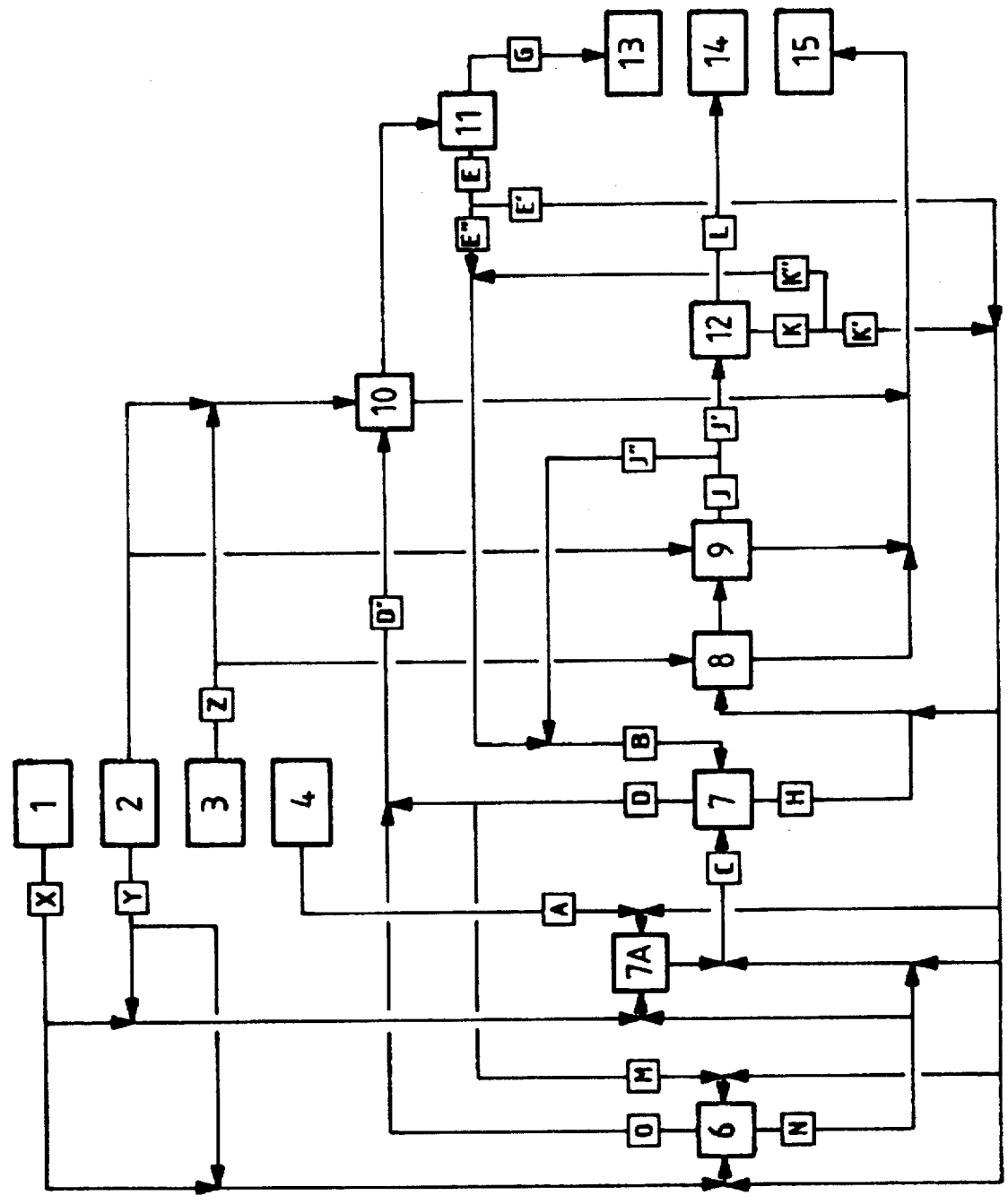
Figure 3:
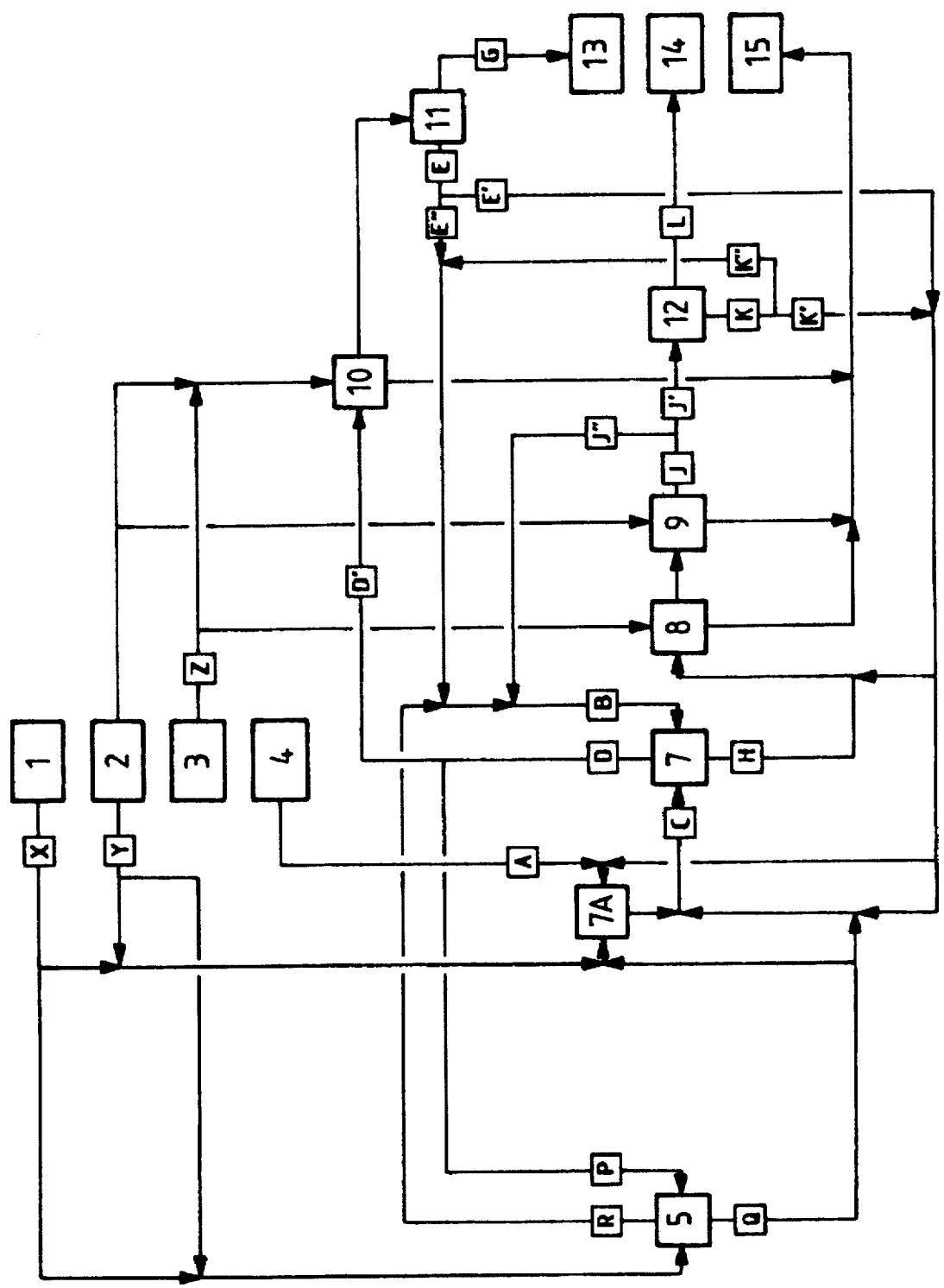
Figure 4:
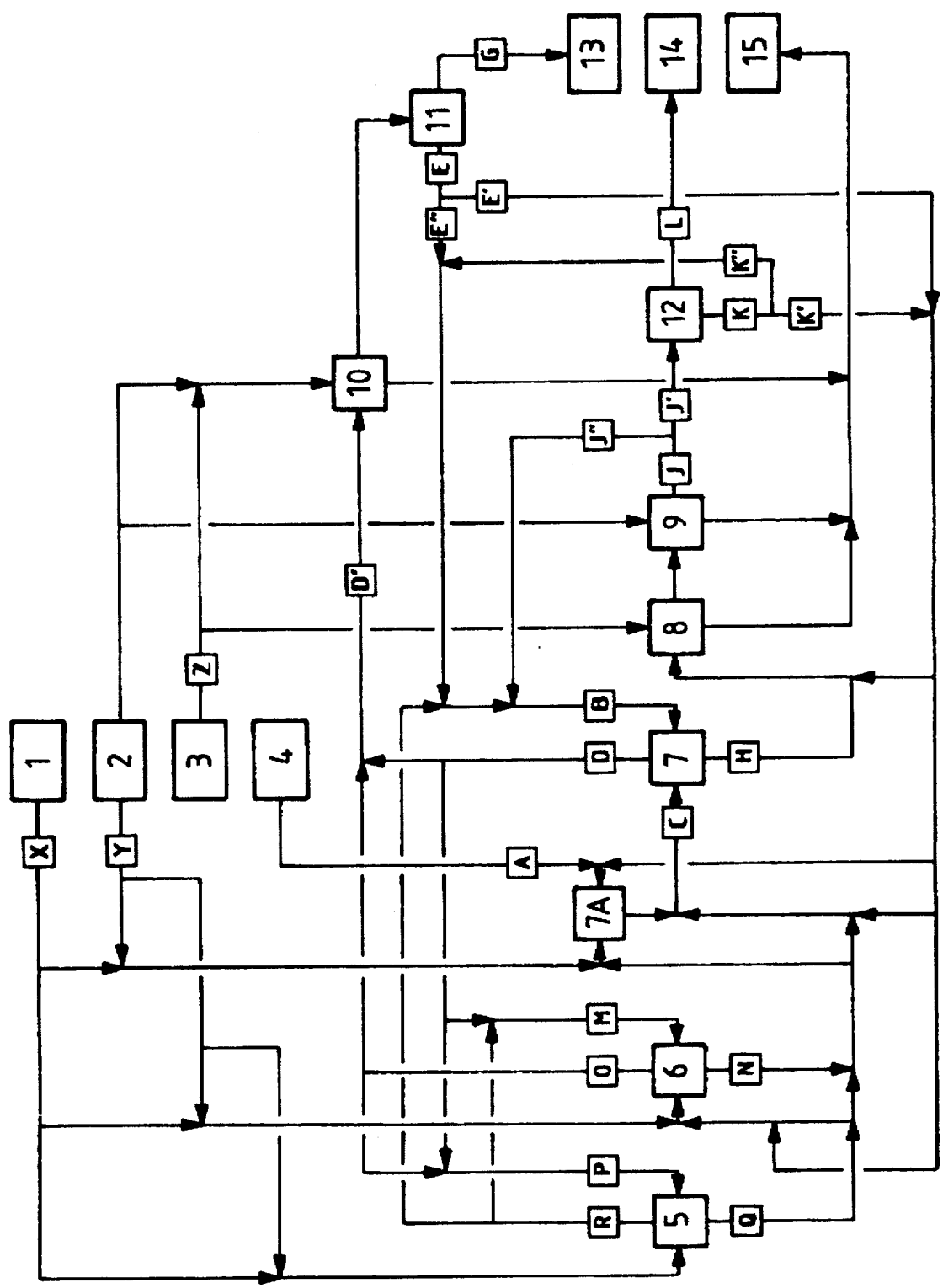

The process according to the invention can be carried out with one extraction stage (FIG. 1 ), two extraction stages (FIGS. 2 and 3) or three extraction stages (FIG. 4).

In order to increase the enrichment or corresponding depletion effect, the process according to the invention can be repeated with each of the product fractions obtained.

The flow charts shown in FIGS. 1 to 4 serve to illustrate the process according to the invention in greater detail. In these FIGS.:

(1) is a tank for aqueous acid
(2) is a tank for water
(3) is a tank for aqueous base
(4) is a tank for starting polyamine
(5) is normally a single-stage or multistage extractor whose first and possibly only stage, as far as the aqueous phase is concerned, consists of a mixer-separator unit or, in the extreme case, of a mixer only
(6) is an (intermediate) extraction stage
(7A) is a mixer (7) is an (additional) extraction stage (8) is a neutralization stage (9) is a washing stage

(10) is a washing and/or neutralization stage

(11) is a first distillation stage optionally operated as a multiple stage

(12) is another distillation stage optionally operated as a multiple stage

(13) is a tank for a first process product

(14) is a tank for another process product

(15) is a tank for waste water

The reference letters A–R, X, Y and Z denote the streams to which reference is made below and in the Examples.

In the simplest case the extraction stage (5) is a mixer-separator unit acting as a single stage, although it is preferable to use extraction units acting as multiple stages, the first stage, as far as the stream (X) is concerned, normally consisting of a mixer-separator unit.

In the simplest case the extraction stage (6) is a mixer-separator unit acting as a single stage, although it is preferable to use extraction units acting as multiple stages.

The stage (7A) is a mixer.

In the simplest case the extraction stage (7) also consists of a mixer-separator unit, although here again it is preferable to use extraction units acting as multiple stages.

The extraction units acting as multiple stages can consist of several extractors connected in series. It is preferable to use the conventional countercurrent extraction devices.

The neutralization stage (8) is a device for the intensive mixing of the aqueous phases (H) for reaction of the acid present with an excess of the aqueous solution of a strong base (Z) from the tank (3), with the possibility of dissipating heat of neutralization, and subsequent separation of the polyamine.

The thorough mixing is effected in the simplest case using one or more stirred vessels, it being possible for the mixing process to be improved by means of mixing nozzles, intensive mixers and/or recirculating devices. The subsequent phase separation is effected in the simplest case using separators, it being possible for the phase separation to be improved by the incorporation of separating aids. Centrifuges, for example, are also suitable.

In cases where simple mechanical separation, after the reaction of the aqueous phases (H) with strong bases, is difficult or impossible, the separation is carried out using additional auxiliary amine or, if appropriate, water, optionally as an extraction process in an extractor preferably acting as a multistage extractor.

In the simplest case the washing stage (9) is a mixer-separator unit in which the stream (J) is washed with water; the washing stage (9) is basically unnecessary, although normally advantageous, for carrying out the process according to the invention.

In the simplest case the washing and/or neutralization stage (10) is also a mixer-separator unit, although it is preferable to use extractors acting as multistage extractors.

In the process stage (10) the organic phase (D) can be reacted and freed of acid with water or, preferably, with dilute aqueous solutions of strong bases.

If the process stage (10) is operated purely as a washing stage using water, the resulting aqueous phase, after it has been separated off, is not added to the waste water but recycled into the process at a suitable point.

In the simplest case the distillation stages (11) and (12) each consist of a distillation column in which each of the respective feed products is separated into a distillate fraction, consisting of auxiliary amine, and the distillation residue, consisting of a first polyamine fraction (G) in the case of the distillation stage (11) and a second polyamine fraction (L) in the case of the distillation stage (12).

The use of an energetically more favorable multistage distillation in the stage (11) and/or (12) is particularly preferred when the additional technical costs associated therewith are economically justified. The distillates obtained can be combined and mixed together before being reused.

If the neutralization stage (8) is operated with the concomitant use of additional auxiliary amine as solvent, the feed product entering the distillation stage (12) normally contains appreciable proportions of auxiliary amine, which are generally separated together as the distillate fraction (K) from the second polyamine fraction (L) obtained as the distillation residue.

The process according to the invention can be carried out in several technical variants. According to a first variant, the starting polyamine mixture (stream A) is fed from the tank (4) into the process stage (7).

The stage (7A) which may be present serves to relieve the extraction stage (7) and consists, in the simplest case of the first variant of the process according to the invention, of a mixer upstream of the stage (7), in which the actual stream (C) is formed and adjusted from aqueous acid (stream X), optionally water (stream Y) for adjusting the acid concentration as desired, and/or optionally auxiliary amine.

It has proved advantageous also to mix at least part of the starting polyamine (A) with the constituents of the stream (C) in the mixer (7A) and to feed the resulting aqueous phase into the extraction stage (7) as the stream (C), which normally consists of water, a strong acid, polyamine and optionally auxiliary amine.

The acid is generally present in the aqueous phase (C) as an aqueous solution of the acid, which optionally contains ammonium salts of the acid with polyamine and/or auxiliary amine; the acid is preferably present as an aqueous solution of its ammonium salts with polyamine and/or auxiliary amine, which optionally contains, in solution, free polyamine and/or auxiliary amine, i.e. polyamine and/or auxiliary amine not bound in the form of salts.

It is then perfectly possible, and perhaps also advantageous for solving a special separation problem, to feed the stream (C) into the stage (7) entirely without auxiliary amine, with the proviso of satisfying the boundary condition which applies in every case to the process stage (6), namely that the sum of the amine equivalents introduced into the streams (A), (B) and (C) always exceeds the number of acid equivalents introduced into the stream (C).

It has proved convenient to define the acid content of the aqueous phase by means of a so-called "molarity", independently of the amine content which appears in the aqueous phase of a two-phase system as a function of process parameters (e.g. composition of organic and aqueous phases, phase ratio, temperature). The "molarity" is established as the theoretical concentration of 100% protonated amine (i.e. the same number of acid and amine equivalents) in a volume of aqueous phase mathematically reduced by the proportion of non-protonated amine, or, if appropriate, in a volume of aqueous phase mathematically increased by an appropriate amount of amine up to complete binding of the acid as ammonium salts.

As an important control variable, the acid content of the stream (C), which is well defined for the particular embodiment of the process according to the invention and is measured and regulated within narrow limits, is varied over a wide range in the process as a whole or specifically in individual process stages, depending on the separation task—in this case product-related—on which the particular embodiment is based, optionally with the addition of water from the stream (Y) or aqueous acid from the stream (X).

At the upper end this working range is limited in practical terms on the one hand by the increasing tendency of the amine salts to crystallize with increasing concentration, and on the other hand by the increasing mutual solubility of the phases in one another.

As far as molarity is concerned, the working range of the process according to the invention is limited at the bottom end by economic considerations. Due to the decreasing acid content, the separation efficiency drops quantitatively, i.e. with outstanding qualitative separation efficiency and without technical problems, a drop in molarity means that an increasingly large volume of aqueous phase is required in order to separate a given amount of amine.

In the extraction stage (7), which is preferably operated as a multiple stage, the organic phase (B) and the aqueous phase (C) are circulated in countercurrent, with thorough intimate mixing.

In this process there is normally a transfer of polyarylamine from the aqueous phase (C) to the organic phase (B), optionally in exchange for arylamine in the opposite direction.

In the aqueous phase (H) leaving the extraction stage (7), the acid is in the form of an aqueous solution of its ammonium salts with polyamine and optionally auxiliary amine, which normally also contains, in solution, free polyamine, i.e. polyamine not bound in the form of a salt, and optionally free auxiliary amine, i.e. auxiliary amine not bound in the form of a salt.

The organic phase (B) generally consists of auxiliary amine and/or polyamine, the latter preferably having the composition of the second process partial product (L).

When the process according to the invention is carried out, the stream (B) is formed in the simplest case of the distillate stream (E) from the distillation stage (11), which in this case is optionally a single stage. In practical terms, the stream (E) consists in this case of auxiliary amine. The efficacy of the process stage (7) is linked in this case solely to a sufficiently large excess of the total amine equivalents over the acid equivalents in the aqueous phase introduced.

Because of the increased tendency of the ammonium salts of the polyamines to crystallize, the extraction stage (7) is normally operated at elevated temperatures, preferably at temperatures above 80° C., and optionally under pressure.

The starting polyamine (A) introduced together with the aqueous phase (C) into the extractor (7) divides up into the aqueous phase (H) leaving the extractor and the organic phase (D) leaving the extractor (7) (quantitative fractionation).

The quantitative division of the individual components of the starting polyamine mixture into the resulting aqueous phase (H) and the resulting organic phase (D), under the conditions of the process according to the invention, takes place with a surprisingly high selectivity, such that the resulting product fractions have a different composition, which under certain circumstances differs greatly from that of the starting polyamine mixture (qualitative fractionation).

For example, starting from the preferred aniline/formaldehyde condensation products, it was found that normally the ortho isomeric form(s) of a polyamine component present in two or more isomeric forms in the starting mixture is (are) relatively enriched in the organic phase (D) leaving the separation stage (7), an example being 2,4'-diaminodiphenylmethane relative to 4,4'-diaminodiphenylmethane. Conversely, the resulting aqueous phase (H) is relatively depleted in the 2,4'-isomer while the 4,4'-isomer is relatively enriched.

If several "ortho isomers" are present in the starting polyamine, e.g. 2,2'- and 2,4'-diaminodiphenylmethane, then the "ortho-richer" 2,2'-isomer is more highly enriched in the organic phase (D) than the "ortho-poorer" 2,4'-isomer, the latter in turn being relatively enriched compared with the even "ortho-poorer" 4,4'-isomer.

The enrichment and depletion effect first found in the aniline/formaldehyde condensation products of the diaminodiphenylmethane series was associated with the criterion of ortho and para substitution as a purely empirical description. The derived characterization of the process products as "ortho-rich" and "ortho-poor" is relative and was expressed by the concept of "degree of ortho substitution".

The "degree of ortho substitution" is defined here as the ratio of the ortho position amino group/methylene group relationships to the total number of all amino group relationships. This concept makes it possible to cover practically all isomer separations which involve polyamines prepared from arylamines, including substituted arylamines, with carbonyl compounds in aqueous-acidic media.

Surprisingly, the same enrichment and depletion effect—in order of degree of ortho substitution—has now also been found for the well-characterized and analytically detectable isomeric trinuclear compounds from the aniline/formaldehyde condensation. The same applies to the separation of condensation products of formaldehyde with aniline and diaminoaryl compounds such as phenylenediamine or alkyl-substituted phenylenediamines.

As a result of their preparation, the polyamine mixtures mentioned hitherto have amino groups which are practically only in the ortho position and/or para position relative to methylene groups. Within a group of isomeric compounds, the fractionation in the organic phase (D) normally enriches those with the higher degree of ortho substitution relative to the isomers with a lower degree of ortho substitution.

Mixtures of polyamines, especially of the diphenylmethane series, including the corresponding higher-nuclear homologues, which are prepared by other processes, for example by the nitration of diphenylmethane or methyldiphenylmethanes and subsequent reduction, also have amino group/methylene group relationships other than amino groups in the ortho and para positions, due to their preparation. The process according to the invention is just as effective for these polyamine mixtures.

For example, a mixture of 2- and 4-methyldiphenylmethane can be nitrated and then reduced to give a polyamine mixture which mainly consists of an isomer mixture of In the fractionation of such mixtures using the process according to the invention, the 3,2'-amino isomers in the organic phase (D) are enriched relative to the 3,4'-amino isomers.

The criterion "ortho-rich" and "ortho-poor" or the "degree of ortho substitution" no longer covers all the isomers in these polyamine mixtures and therefore has to be applied by analogy: instead of the concepts "in the ortho position" and "in the para position", the isomers are divided into those (ortho) with a smaller distance and those (para) with a larger distance between the amino groups (normally located on different six-membered rings) and the methylene bridge or between the amino groups themselves.

A further class of mixtures of aromatic polyamines which can be fractionated very effectively using the process according to the invention comprises the polyamines of triphenylmethane and its higher-nuclear homologues, preferably benzyl homologues, such as e.g. those prepared by the nitration and subsequent reduction of the corresponding hydrocarbon mixtures.

In the fractionation of technical-grade polyamine mixtures of the last-mentioned classes of substances:

I. mixed condensation products of monoaminoaryl and diaminoaryl compounds with formaldehyde or carbonyl compounds in general, II. polyamine mixtures from processes involving the nitration and subsequent reduction of diphenylmethane and preferably substituted, especially alkyl-substituted, diphenylmethanes and the corresponding homologues, and III. polyamine mixtures from processes involving the nitration and subsequent reduction of triphenylmethane and preferably substituted, especially alkyl-substituted, triphenylmethanes and the corresponding higher-nuclear benzyl homologues, a surprising selectivity was found in addition to a clean separation of the isomers.

Polyamine mixtures of said classes of substances I to III contain or can contain components in which at least one aryl ring per molecule carries more than one and normally two amino groups. These components can be the preferred constituents of the polyamine mixture without having to be the major products in quantitative terms as a condition of the process.

Such components are better characterized by using the concept of "degree of amino substitution", which indicates primarily the number of amino groups in a component relative to the number of aryl rings. For aniline and its condensation products with formaldehyde, this expression is always 1.0; for phenylenediamine and its condensation products, it is always 2.0. In the case of pure mixed condensation products, the diphenylmethane isomers have a value of 1.5 and the higher-nuclear homologues have values of between >1.0 and <2.0. If the concept of degree of amino substitution is used statistically for characterizing technical-grade polyamine mixtures, the values obtained are again between 1.0 and 2.0.

In the fractionation of polyamine mixtures with a degree of amino substitution of >1.0, it has now been found that the components with a higher degree of amino substitution are relatively enriched in the resulting aqueous phase (H), said enrichment increasing with the degree of amino substitution.

In the case of polyamine mixtures prepared by the nitration and subsequent reduction of polyaryl systems with three or more aryl rings, it is possible to form polyamine components with a degree of amino substitution of <1 which are also amenable to fractionation by the process according to the invention.

Independently of this, the separation according to the "degree of ortho substitution" is effective here as well.

Thus, for this class of substances too, the process according to the invention opens up new ways of disassociating the production form of the raw materials (amine stage) from the use form of the end products (isocyanate stage) by fractionation and/or enrichment at the amine stage and separate further processing of the fractions, so as to facilitate separate optimization of both stages up to the point of obtaining completely novel isocyanate mixtures, or so as to make it possible for the first time where suitable processes and methods were lacking hitherto or are of little practicability.

These "achievements" are further complemented by a selectivity criterion, which was found in the fractionation of technical-grade polyamine mixtures, especially those with higher-nuclear homologues, and relates to the "nuclearity" of the polyamine mixtures. The concept of "nuclearity" primarily expresses the number of aryl units in a component of a mixture of aromatic polyamines. In the broader sense, the concept of nuclearity is used statistically to express a nuclearity of the whole mixture in the case of a polyamine mixture consisting of numerous components with individually exact but different nuclearities.

Particularly surprisingly, it has now been found, in the fractionation of polyamine mixtures with higher-nuclear constituents, especially in the fractionation of technical-grade mixtures of aniline/formaldehyde condensation products, that such mixtures can also be fractionated according to the criterion of nuclearity.

In particular, a low molarity of the aqueous phase (C) within the molarity range usable in the process leads to a relative enrichment of higher-nuclear components in the organic phase (D).

The surprising result can be extended and stated in precise terms by saying that the relative enrichment and depletion also takes place among the higher-nuclear homologues. If, for example, in a technical-grade mixture of diaminodiphenylmethane, there is a relative enrichment or depletion of the trinuclear components compared with the dinuclear components in the one fraction, a similar relative enrichment or depletion of tetranuclear components compared with trinuclear components, i.e. an even greater relative enrichment or depletion, is also found, the same applying to pentanuclear components compared with tetranuclear components, etc.

This fact, the isomer separation which takes place simultaneously and always in the sense of a relative increase in the "degree of ortho substitution" in the organic phase (D), and the ability to repeat the separation according to the invention on individual product fractions, optionally with altered process parameters, give rise to numerous possibilities of starting from known and readily accessible polyamine mixtures and, via the process according to the invention, obtaining polyamines and hence polyisocyanates which are less readily accessible or completely novel, being hitherto inaccessible according to the state of the art. This applies particularly to products of the diaminodiphenylmethane and diisocyanatodiphenylmethane series and very particularly to polyamine and polyisocyanate mixtures with an extremely high proportion of higher-nuclear components.

The enrichment or depletion normally becomes more effective with increasing degree of protonation in the aqueous phase of the separation stage.

The degree of protonation represents the ratio of acid equivalents to amine equivalents.

Furthermore, the process according to the invention proves to be generally effective on other structurally related polyamines as well. Thus, for example, the above mentioned polyamine mixtures obtained by the nitration of diarylmethanes and polyarylmethanes and subsequent reduction can also contain monoaminopolyarylmethane compounds or components in which one or more methylene groups have been converted by secondary reactions to keto and/or hydroxymethylene groups and hence to undesirable by-products.

Numerous incompletely rearranged intermediates and by-products can occur in the condensation of arylamines with carbonyl compounds. Most of these compounds, in the fractionation of the polyamine mixtures containing them, normally undergo enrichment in one of the resulting fractions, so the effect can be utilized for separation and fractionation.

Optionally, such products can be enriched in this way or they can be fractionated as specifically prepared polyamine mixtures, e.g. polyaminobenzophenones or aminobenzylarylamine mixtures.

Depending on the auxiliary amine used, the organic phase (D) leaving the extraction stage (7) contains inter alia variable amounts of acid, which are removed before the stream (D) is worked up by distillation.

In the simplest case this takes place in the process stage (10) by washing with water and/or by neutralization with an excess of dilute aqueous bases, for example dilute sodium hydroxide solution.

After passing through the stage (10), the organic phase (D) or (D') is transferred to the distillation stage (11).

In the last stage of the optionally multiple distillation stage (11), the first polyamine partial product (G) is separated off and collected in the process product tank (13).

The corresponding second partial product is in the aqueous phase (H) leaving the extraction stage (7).

Optionally after the addition of auxiliary amine, the aqueous phase (H) is reacted in the neutralization stage (8) with an aqueous solution of a strong base, preferably sodium hydroxide solution, in order to neutralize the acid present.

The aqueous phase formed in the neutralization is separated off and collected in the waste water tank (15).

The organic phase formed in the neutralization is separated off as the stream (J), optionally washed with water in the washing stage (9) and then worked up by distillation (12).

In the last stage of the optionally multiple distillation stage (12), the second polyamine partial product (L) is separated off and collected in the process product tank (14).

This first variant of the process according to the invention makes it possible to achieve considerable separation efficiencies in the fractionation of polyamine mixtures and satisfactorily to solve numerous separation problems.

Especially in the second polyamine fraction (L), the relative enrichment of the component preferentially contained in this fraction can be specifically varied and maximized.

In this first Variant, however, the proportion of these components remaining in the first polyamine fraction (G) cannot be minimized in the same way, but can variably be relatively depleted only down to a content whose lower limit depends on the partition equilibrium of the polyamine components of (A) between the organic phase (D) leaving the extractor (7) and the aqueous phase (C) entering the extractor (7), said partition equilibrium being characteristic of the particular process parameters.

The organic phase (B) generally consists of auxiliary amine and/or polyamine, the latter preferably having the composition of the second process partial product (L).

When using an organic phase (B) without polyamine, the polyamine fraction which results in the aqueous phase (H) leaving the extraction stage (7) is one in which the relative enrichment of the components preferentially contained in this phase can be specifically increased and maximized, at the expense of the polyamine concentration in the aqueous phase.

The effect of polyamine as a constituent of the organic phase (B) is that the phase (H) leaving the process stage (7) has a higher polyamine concentration, which is thus energetically more advantageous for carrying out the process according to the invention, than when using an organic phase (B) without polyamine.

Through the preferred use of a polyamine having the composition of the second partial product (L) as a constituent of the organic phase (B), the relative enrichment of the polyamine components preferentially contained in the aqueous phase (H) leaving the separation stage (7), and hence of the second polyamine fraction (L), can also be varied and maximized to a higher and therefore advantageous concentration level as a result of equilibrium adjustment with accumulation of the separation effect.

More advantageous, and preferred as an embodiment, is a second variant of the process according to the invention, in which, in the first polyamine fraction (G) as well, the relevant enrichment of the components preferentially contained in this fraction can additionally be appreciably increased and specifically varied in that the organic phase (D) obtained in the extraction stage (7) is at least partially extracted, in an extraction stage (6) (which is an intermediate stage as far as the phase (D) is concerned) with an aqueous phase which, in the present case of variant 2, consists essentially of at least part of the stream (X), optionally additional water from the stream (Y) and optionally auxiliary amine.

For formal reasons, the organic phase fed into the extraction stage (6) is denoted as the stream (M), even though, as explained in the present case by way of example, it may be identical to the stream (D), at least in terms of composition, but preferably also in terms of amount.

Even when the extraction stage (6) is operated as a single stage, for example as a mixer-separator unit, the resulting organic phase (O) shows, according to the type and amount of the aqueous phase used, a marked additional relative enrichment of the components already enriched in (D) compared with starting polyamine (A), and correspondingly shows a drop in its polyamine content in the resulting organic phase (O). Preferably, however, because of the improved efficacy, the intermediate extraction stage (6) is also designed as an extractor acting as a multistage extractor and operated in countercurrent.

The aqueous phase (N) obtained in the extraction stage (6) contains the other, corresponding fraction of the polyamine introduced with the stream (M), in which fraction the components enriched in (O) are correspondingly depleted. The extent of the relative depletion, i.e. the composition of the polyamine contained in (O), is controlled, under the particular process conditions of the extraction stage (6) acting as a multiple stage, by the qualitative and quantitative partition equilibrium between the incoming organic phase (M) and the outgoing aqueous phase (N).

Depending on the separation task, the molarity of the aqueous phase in the extraction stage (6) is higher than, equal to or lower than the molarity in the extraction stage (7), which is downstream as far as the aqueous phase is concerned, and is regulated by the addition of acid and/or the addition or, if appropriate, withdrawal of water at a suitable point.

Optionally after the addition of water, the aqueous phase (N) resulting from the process stage (6) is fed into the extraction stage (7), together with any remaining (X) which may be present.

The organic phase (O) resulting from the stage (6) is fed into the distillation stage (11), together with any remaining (D) which may be present, in order to obtain the polyamine fraction (G).

The second variant of the process according to the invention makes it possible specifically to vary and maximize the relative enrichment in both the resulting polyamine fractions. Apart from this qualitatively high level of versatility and efficiency, the second process variant also represents an energetically favorable embodiment, at least for the second polyamine fraction (L).

The third variant of the process according to the invention represents an improved embodiment for the partial product (G) in energy terms. The first variant, which is taken as the basis, is extended to the effect that the organic phase (D) leaving the process stage (7), which contains the first partial product (G) in reduced concentration compared with the concentration of (A) in (C), is divided into a stream (D'), which is subsequently fed into the working-up stages (10) and (11) in order to obtain the polyamine fraction (G), and a stream (P).

In an upstream extraction stage (5), the stream (P) is reacted with at least part and preferably all of the aqueous acid available as the stream (X); the reaction is optionally carried out as a multistage countercurrent extraction.

The extraction stage (5) is normally an extractor, acting as a multistage extractor and operated in countercurrent, in which the incoming organic phase (P) is extracted with at least part and preferably all of the aqueous acid (X) available for re-use.

Here the stream (P) fed into the extractor (5) is proportioned so that, in the reaction with the stream (X), the transfer at least of the polyamines contained in the organic phase (P) into the aqueous phase (Q) leaving the extractor (5) is as extensive as possible and preferably practically quantitative.

If the sum of the acid equivalents introduced into the process stage (5) exceeds that of the amine equivalents, the transfer of the amines into the aqueous phase is practically quantitative, even in a single process stage, so no organic phase (R) results. The presence of free acid in the resulting aqueous phase is of no importance for the continuation of the process.

Also in the case of an excess of the amine equivalents in (P) over the acid equivalents in (X), and even in the case of a limited excess of the polyamine equivalents in (P) over the acid equivalents in (X), an organic phase (R) which is sufficiently depleted in polyamine in the sense of the process according to the invention can be obtained by operating the upstream process stage (5) as a multiple stage and working in countercurrent.

The residual content of polyamine in the organic phase (R) leaving the process stage (5) is generally <3 wt. %, preferably <1 wt. %. Furthermore, the maximum amine content permissible in (R) and, in particular, the polyamine content depend on the qualitative demands on the process products—especially on the process partial product (L) in the case of variant 3—resulting from the separation task in question. Maintenance of the polyamine content relevant to the quality of (L) is controlled by proportioning the partial stream (P), within the limits of the technical conditions, with exhaustion of the available aqueous acid (X) and optionally of a quantity of (Y).

The fact that the amount of aqueous acid available for use in the stage (5) (stream X) is proportional to the amount of the second polyamine fraction (L) and consequently inversely proportional to the amount of the first polyamine fraction (G) comes in useful for the process and especially for the extraction stage (5). A small polyamine fraction (G) normally means a low polyamine concentration in the organic phase (D) and a high energy expenditure in the working-up of such a phase. Variant 3 according to the invention makes it possible especially to reduce the energy expenditure in the isolation of the first polyamine fraction (G), compared with variant 1.

The contribution of the process stage (5), in the context of variant 3, towards improving the process according to the invention is that the distillative working-up (11) for obtaining the first polyamine fraction (G) is carried out not on the total stream, with a relatively low and hence energetically unfavorable concentration of polyamine, but only on a partial stream, with a correspondingly higher and hence energetically more favorable concentration (quantitative enrichment), while an organic phase (R), usable as an extraction agent at a suitable point, is obtained from the other partial stream without distillation.

The organic phase (R), which leaves the process stage (5) essentially freed of polyamine, is fed into the extraction stage (7).

In the extraction stage (7), which preferably acts as a multiple stage, the organic phase (R) is added as extraction agent, normally by mixing with the stream (B) and introduction into the first stage of the extractor, as far as the organic phase (B) is concerned.

As a function of a residual polyamine content which may be present in (R), and considering the quality of the second polyamine fraction (L), the organic phase (R) is optionally introduced into a later stage, as far as the organic phase (B) is concerned, or optionally into the last stage of the extraction stage (7) operating as a multiple stage.

In addition to the acid present at least partially in the form of its ammonium salts, the aqueous phase (Q) leaving the process stage (5) contains polyamine with a composition corresponding essentially to the polyamine in the incoming organic phase (P), and optionally auxiliary amine.

In the case of variant 3 of the process according to the invention, the stream (Q) is fed directly into the process stage (7), optionally after the addition of water from the stream (Y) and/or of further aqueous acid from the stream (X).

As the polyamine fraction contained in the aqueous phase (Q) normally exhibits a higher relative (qualitative) enrichment in terms of the first polyamine fraction (G) compared with the starting polyamine (A), the result for the aqueous phase fed into the extraction stage (7), after the addition of starting polyamine (A), is a mixed polyamine which is "enriched" compared with the latter as a function of the quantitative proportion. As a consequence of the partition equilibrium between the incoming aqueous phase and the resulting organic phase (D), variant 3 also offers a limited additional qualitative enrichment effect for the first polyamine fraction (G).

In a further variant of the process according to the invention, variant 4, the technical measures of the previous variants are brought together and combined with one another.

In the simplest case the extraction stages (5) and (6) are added and each one is operated individually, in the described manner, with a partial stream of (X), optionally a partial stream of (Y) and a partial stream of (D), which in this case is Optionally divided into three partial streams.

As the organic phase (P) in the extraction stage (5), it is more advantageous to use a partial stream of the stream (O), which contains a qualitatively highly enriched and quantitatively less concentrated polyamine fraction.

Variant 4 is preferably carried out so that a partial stream of (D) and/or, preferably, a partial stream of (O) are used as the organic phase (P) in the extraction stage (5), and so that at least part and preferably all of the aqueous phase (Q) resulting from the stage (5) is fed into the extraction stage (6) and used in (6), optionally with the addition of further aqueous acid from the stream (X) and optionally with the addition of auxiliary amine. Here the organic phase (M), with its content of similarly enriched polyamine, is circulated in countercurrent with said aqueous phase (Q) in several stages, with intimate thorough mixing; the organic phase (M) is optionally augmented by the addition to (M) of a partial stream of the organic phase (R) resulting from the extraction stage (5).

These measures produce a further increase in the qualitative enrichment effect in the organic phase (O) resulting from (6). In quantitative terms, this result can be achieved by proportioning and dividing the streams for a relatively high and hence energetically favorable polyamine content in the phases resulting from (6), especially in the organic phase (O).

The feedback of the enrichment effect in (O) via the stream (P), which is a partial stream of (O), and via the aqueous phase (Q) has a cumulative action.

As a result of the design and interconnection, according to the invention, of the extraction stages (5) to (7) in variant 4, with process criteria such as disproportionation instead of fractional extraction in the stage (6), accumulation through interconnection with the extraction stage (5) and recovery of extractant in the stage (5), without distillation, for use in the process stage (7) and optionally in (6), the maximum qualitative separation efficiency is achieved, which, in combination with the variation in the molarity of the aqueous phases in the stages (5) to (7), gives the process according to the invention a wide range of applications.

The invention is further illustrated but is not intended to be limited by the following examples in which all parts and percentages are by weight unless otherwise specified.

EXAMPLES

Example 1

In a mixer (7A), the starting polyamine mixture (stream A) (1.900 kg/h) is mixed with 1.400 kg/h of 30% hydrochloric acid (stream X) and 2.700 kg/h of water (stream Y) to form the stream (C).

| Stream (C) | 31.7% of polyarylamine |
|---|---|
| (6.000 kg/h) | 7.0% of hydrogen chloride |
|  | 61.3% of water |

In an extractor (7) acting as a multistage extractor, the stream (C) is circulated at 85° C. in countercurrent with the organic stream (B) [7.200 kg/h], which consists essentially of 2,6-dimethylaniline.

The resulting organic phase leaving the extraction stage (7) (stream D) has the following average composition:

| Stream (D) | 12.0% of polyarylamine |
|---|---|
| (7.600 kg/h) | 87.3% of 2,6-dimethylaniline |
|  | 0.2% of hydrogen chloride |
|  | 0.5% of water |

The stream (D) is reacted in the neutralization stage (10) with excess dilute sodium hydroxide solution (partial stream of Z) and water from the tank (2). The aqueous phase is collected as waste water in the tank (15).

In the downstream distillation stage (11), the washed stream (D), freed of acid residues, is separated into a distillate fraction (E) of 6.635 kg/h, which consists essentially of 2,6-dimethylaniline, and a distillation residue, which is collected in the tank (13) as the stream (G) of 0.910 kg/h and represents the first polyamine fraction.

The distillate (E) is used to form the stream (B) and is fed into the extraction stage (7).

The aqueous phase (H) leaving the extractor (7) has the following composition:

| Stream (H) | 17.7% of polyarylamine |
|---|---|
| (5.600 kg/h) | 10.1% of 2,6-dimethylaniline |
|  | 7.2% of hydrogen chloride |
|  | 65.0% of water |

The stream (H) is neutralized in the downstream neutralization stage (8) with excess aqueous sodium hydroxide solution from the tank (3) (bulk of the stream Z). The aqueous phase containing salts is separated off and collected in the waste water tank (15).

The organic phase is then washed in the washing stage (9) with water from the tank (2) until it is free of salts. The wash water is also collected in the waste water tank (15).

The organic phase leaving the washing stage (stream J) is separated in the distillation stage (12) into a distillate fraction (K) and a distillation residue (L).

The stream (K) (0.565 kg/h) consists essentially of 2,6-dimethylaniline and is fed into the extraction stage (7) to form the stream (B).

The stream (L) of 0.990 kg/h represents the second polyamine fraction and is collected in the tank (14).

| Polyarylamine GC: | A [wt. %] | G [wt. %] | L [wt. %] |
|---|---|---|---|
| 2,2'-Diaminodiphenylmethane | 0.3 | 0.6 | — |
| 2,4'-Diaminodiphenylmethane | 5.4 | 11.4 | 0.1 |
| 4,4'-Diaminodiphenylmethane | 62.8 | 52.7 | 69.9 |
| N-Methyl-4,4'-diaminodiphenylmethane | 0.1 | 0.2 | — |
| Σ Diaminodiphenylmethanes | 68.6 | 64.9 | 72.0 |
| Σ Polynuclear polyamines | 31.4 | 35.1 | 28.0 |
| Quantitative distribution | 100% | 48.0% | 52.0% |

Example 2

In a mixer (7A), the starting polyamine mixture (stream A) (1.445 kg/h) and the aqueous phase leaving the extractor (5) (stream Q) (6.000 kg/h) are mixed together to form the stream (C).

| Stream (C) | 25.6% of polyarylamine |
|---|---|
| (6.000 kg/h) | 19.3% of 2,6-dimethylaniline |
|  | 5.6% of hydrogen chloride |
|  | 49.5% of water |

In an extractor (7) acting as a multistage extractor, the stream (C) is circulated at 85° C. in countercurrent with the organic stream (B), which consists essentially of 2,6-dimethylaniline.

The stream (B) is composed of the stream (R), i.e. the organic phase leaving the extractor (5) (2.100 kg/h), and the two distillate streams (E) and (K) [Streams (E)+(K)=4.055 kg/h].

Here the part consisting of the distillates (E) and (K) is introduced into the first stage, as far as the organic phase (B) is concerned, of the extractor (7) comprising a total of 10 stages, and the part consisting of the stream (R) is introduced into the third stage, as far as the organic phase (B) is concerned, of the extractor (7).

The organic phase resulting from the stage (7) (stream D) has the following average composition:

| Stream (D) | 11.4% of polyarylamine |
|---|---|
| (8.000 kg/h) | 87.9% of 2,6-dimethylaniline |
| | 0.2% of hydrogen chloride |
| | 0.5% of water |

A partial stream (stream P) of ca. 4.0 kg/h is separated from the organic phase (D) and fed into the upstream extraction stage (5).

The residual stream (D') is reacted in the neutralization stage (10) with excess dilute sodium hydroxide solution (partial stream of Z) and water from the tank (2). The resulting aqueous phase is separated off and collected as waste water in the tank (15).

In the downstream distillation stage (11), the washed stream (D'), freed of acid residues, is separated into a distillate fraction (E) of 3.535 kg/h, which consists essentially of 2,6-dimethylaniline, and a distillation residue, which is collected in the tank (13) as the stream (G) of 0.455 kg/h and represents the first polyamine fraction.

The distillate (E) is used to form the stream (B).

In an upstream extraction stage (5), the partial stream separated from (D) as the stream (P) is circulated in countercurrent with an aqueous phase made up of 1.400 kg/h of 30% hydrochloric acid (stream X) and 2.700 kg/h of water (stream Y).

The first stage, as far as the aqueous phase is concerned, of the stage (5), which is designed as a multistage extractor, consists of a mixer made of a material resistant to hydrochloric acid, with the possibility of dissipating the heat (of neutralization). The stage (5) is otherwise operated at 85°–90° C.

The resulting organic phase (R) (2.100 kg/h) consists essentially of 2,6-dimethylaniline and is used to form the stream (B).

The resulting aqueous phase (Q) has the following average composition:

| Stream (Q) | 7.6% of polyarylamine |
|---|---|
| (6.000 kg/h) | 23.9% of 2,6-dimethylaniline |
| | 7.1% of hydrogen chloride |
| | 61.4% of water | and is fed into the stage (7) to form the stream (C).

The aqueous phase (H) leaving the extractor (7) has the following composition:

| Stream (H) | 17.7% of polyarylamine |
|---|---|
| (5.600 kg/h) | 9.3% of 2,6-dimethylaniline |
| | 7.3% of hydrogen chloride |
| | 65.7% of water |

The stream (H) is neutralized in the downstream neutralization stage (8) with excess aqueous sodium hydroxide solution from the tank (3) (bulk of the stream Z). The aqueous phase containing salts is separated off and collected in the waste water tank (15).

The organic phase is then washed in the washing stage (9) with water from the tank (2) until it is free of salts. The wash water is also collected in the waste water tank (15).

In the distillation stage (12), the organic phase leaving the washing stage (stream J) is separated into a distillate fraction (K) and a distillation residue (L).

The stream (K) (0.520 kg/h) consists essentially of 2,6-dimethyl-aniline and is fed into the extraction stage (7) to form the stream (B).

The stream (L) of 0.990 kg/h represents the second polyamine fraction and is collected in the tank (14).

| Polyarylamine GC: | A [wt. %] | G [wt. %] | L [wt. %] |
|---|---|---|---|
| 2,2'-Diaminodiphenylmethane | 0.3 | 1.0 | — |
| 2,4'-Diaminodiphenylmethane | 5.4 | 16.7 | 0.2 |
| 4,4'-Diaminodiphenylmethane | 62.8 | 43.2 | 71.8 |
| N-Methyl-4,4'-diaminodiphenylmethane | 0.1 | 0.3 | — |
| Σ Diaminodiphenylmethane | 68.6 | 61.2 | 72.0 |
| Σ Polynuclear polyamines | 31.4 | 38.8 | 28.0 |
| Quantitative distribution | 100% | 31.5% | 68.5% |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the fractionation and purification of aromatic polyamine mixtures comprising:
   a) mixing the polyamine starting mixture in a first extraction stage with a two-phase system comprising
      (i) a hydrophobic solvent phase which consists essentially of an aromatic auxiliary amine which is slightly soluble in water and exhibits at normal pressure a boiling point which is at least 20° C. below the boiling point of the lowest-boiling component of the starting mixture, and optionally polyamine, and
      (ii) an aqueous phase consisting essentially of water, a strong acid and optionally an auxiliary amine present at least in part in the salt form, and optionally polyamines present at least in part in the salt form, with said first extraction stage operating on the countercurrent principle, and wherein said polyamine starting mixture is introduced into said first extraction stage with said aqueous phase, with the proviso that the sum of amine equivalents introduced via polyamine mixture, hydrophobic solvent phase and aqueous phase always exceeds the number of acid equivalents introduced via aqueous phase, and with the further proviso that a first aqueous phase and a first organic phase exit said first extraction stage,
   b) distilling said first organic phase in first distillation stage into
      i) a first fraction consisting essentially of auxiliary amine, and
      ii) a distillation residue consisting essentially of a first polyamine fraction,
   c) neutralizing said first aqueous phase by adding a base thereto and phase separating the resultant mixture into
      i) a second aqueous phase containing the acid in the form of its neutral salt, and
      ii) a second organic phase consisting essentially of polyamine and auxiliary amine, and
   d) separating said second organic phase in a second distillation stage into
      i) a distillate consisting essentially of auxiliary amine, and
      ii) a distillation residue consisting essentially of a second polyamine fraction.

2. A process for the fractionation and purification of mixtures of aromatic polyamines wherein
   a) the starting polyamine mixture (A) is partitioned in a two-phase system consisting of (i) a hydrophobic solvent phase (B) consisting essentially of aromatic auxiliary amine, which is sparingly soluble in water and whose boiling point under normal pressure is at least 20° C. below the boiling point of the lowest-boiling component of the starting mixture, and optionally polyamines, and (ii) an aqueous phase (C) consisting essentially of an aqueous solution of a strong acid and optionally auxiliary amine present at least partially in the salt form, and/or optionally polyamines present at least partially in the salt form, with the aid of an extraction stage (7) operating according to the countercurrent principle, and with thorough mixing of the phases, the starting polyamine mixture preferably being introduced into the extraction stage (7) via the aqueous phase (C), with the proviso that, in this two-phase system, the amine equivalents introduced into the streams (A), (B) and (C) are always in excess of the number of acid equivalents introduced into the stream (C), and the organic phase (D) leaving this extraction stage is separated, b) optionally at least partially via an intermediate extraction stage (6) and/or c) optionally with separation of a partial stream before or after passage through the extraction stage (6), if appropriate, and recycling of the separated partial stream, via an upstream extraction stage (5), at least partially into the extraction stage (7), d) after passage through a washing stage and/or neutralization stage (10), in a distillation stage (11), which is optionally operated as a multiple stage, into a distillate fraction, consisting essentially of auxiliary amine, and a first polyamine fraction, obtained as the distillation residue (G), e) the aqueous phase (H) leaving the extraction stage (7) is introduced into a neutralization stage (8), the acid contained in the aqueous phase is neutralized with bases, preferably aqueous sodium hydroxide solution, and the resulting product is then mechanically separated, in a phase separation step, into an aqueous phase, containing the acid in the form of its neutral salts, and an organic phase, containing essentially polyamine and auxiliary amine, and f) the organic phase (J) obtained in the neutralization stage (8) is optionally passed through a washing stage (9) and is at least partially worked up, in an optionally multiple distillation stage (12), into a distillate fraction (K), containing essentially auxiliary amine, and a second polyamine fraction, obtained as the distillation residue (L).

3. The process of claim 2, wherein b) the organic phase (D) obtained in the extraction stage (7) is at least partially extracted in an intermediate extraction stage (6) in countercurrent with at least part of the aqueous acid (stream X) and/or optionally water from the stream (Y) and/or optionally auxiliary amine, and/or extracted in countercurrent with at least part and preferably all of the aqueous phase (Q) obtained in the upstream extraction stage (5), if present, the aqueous phase (N) resulting from the intermediate extraction stage (6) is fed into the extraction stage (7), and the organic phase (O) obtained in the intermediate extraction stage (6) is fed into the working-up stage (11).

4. The process of claim 2, wherein c) a partial stream of the organic phase (D) leaving the extraction stage (7), and/or a partial stream of the organic phase (O) leaving the intermediate extraction stage (6), if present, are separated off and, in an upstream extraction stage (5), reacted in one stage or, preferably, extracted in several stages in countercurrent with at least part of the aqueous acid available as the stream (X), the organic stream (P) used in the extraction stage (5) is proportioned so that, in (5), the greatest possible amount of the polyamine contained in said organic stream (P) passes into the aqueous phase (Q), the aqueous phase (Q) resulting from the upstream extraction stage (5) is fed into the extraction stage (6), optionally after the addition of water from the stream (Y) and/or auxiliary amine, and the polyamine-depleted organic phase (R) obtained in the upstream extraction stage (5) is at least partially fed into the extraction stage (7).

5. The process of claim 2, wherein the auxiliary amine is selected from the group consisting of aniline, anilines substituted on the nitrogen, or anilines substituted on the aromatic ring.

6. The process of claim 2, Wherein the auxiliary amine is 2,6-dimethylaniline.

7. The process of claim 2, wherein the auxiliary amine is 2-methyl-6-ethylaniline.

8. The process of claim 2, wherein the auxiliary amine is N,N-dimethylaniline.

9. The process of claim 2, wherein the auxiliary amine is a mixture consisting of aniline and/or N-alkyl-substituted anilines and/or anilines substituted on the aromatic ring.

10. The process of claim 2, wherein the auxiliary amine is a xylidene mixture.

11. The process of claim 2, wherein the auxiliary amine is a technical-grade alkylation mixture of aniline and derivatives thereof.

12. The process of claim 2, wherein the polyamine starting mixture is a polyamine mixture obtained by acid-catalyzed aniline/ formaldehyde condensation.

13. In a process for the preparation of aromatic polyisocyanates by the phosgenation of aromatic polyamines, the improvement wherein the polyamines are produced according to the process of claim 1.

14. In a process for the preparation of cycloaliphatic polyamines by the hydrogenation of aromatic polyamines, the improvement wherein the aromatic polyamines are produced according to the process of claim 1.

* * * * *